United States Patent
Honda et al.

(10) Patent No.: US 9,531,368 B2
(45) Date of Patent: Dec. 27, 2016

(54) SEMICONDUCTOR SWITCH CIRCUIT, SIGNAL PROCESSING APPARATUS, AND ULTRASOUND DIAGNOSTIC APPARATUS

(71) Applicant: Hitachi Power Semiconductor Device, Ltd., Hitachi-shi, Ibaraki (JP)

(72) Inventors: Hironobu Honda, Tokyo (JP); Fumiaki Yamashita, Tokyo (JP); Junichi Aizawa, Tokyo (JP)

(73) Assignee: Hitachi Power Semiconductor Device, Ltd., Hitachi-shi, Ibaraki (JP)

( * ) Notice: Subject to any disclaimer, the term of this patent is extended or adjusted under 35 U.S.C. 154(b) by 224 days.

(21) Appl. No.: 14/461,382

(22) Filed: Aug. 16, 2014

(65) Prior Publication Data
US 2015/0087990 A1    Mar. 26, 2015

(30) Foreign Application Priority Data
Sep. 24, 2013    (JP) ................. 2013-196862

(51) Int. Cl.
*H03K 17/10* (2006.01)
*A61B 8/00* (2006.01)
(Continued)

(52) U.S. Cl.
CPC ........... *H03K 17/102* (2013.01); *A61B 8/4444* (2013.01); *H03K 17/063* (2013.01);
(Continued)

(58) Field of Classification Search
CPC .... A61B 8/4444; B01D 39/2044; B01J 35/02; B22F 3/002; H03K 17/063
See application file for complete search history.

(56) References Cited

U.S. PATENT DOCUMENTS 5,559,466 A    9/1996  Okumura et al.
6,426,600 B1 *  7/2002  Lautzenhiser .......... G06F 3/012
                                                    180/65.1
(Continued)

FOREIGN PATENT DOCUMENTS

EP    0 637 136 A1    2/1995
JP    S62 240032 A   10/1987
(Continued)

OTHER PUBLICATIONS

European Search Report dated Feb. 10, 2015 for related European application No. 14180728.9.
(Continued)

*Primary Examiner* — Baisakhi Roy
(74) *Attorney, Agent, or Firm* — Miles & Stockbridge P.C.

(57) ABSTRACT

A semiconductor switch circuit comprises: a first switch pair including two MOSFETs having gates connected one another and sources connected to one another, and a zener diode reversely connected between the gates and sources of the MOSFETs; a second switch pair including two MOSFETs having gates connected one another and sources connected to one another, and a zener diode reversely connected between the gates and sources of the MOSFETs; and a third switch pair comprising two MOSFETs having gates connected to one another and sources connected to one another. The first switch pair and the second switch pair are connected in series between two input/output terminals through a connecting node. The third switch pair is connected to the connecting node between the first switch pair and the second switch pair.

10 Claims, 7 Drawing Sheets

COMMENT: ESSENTIAL PART OF ULTRASOUND DIAGNOSTIC APPARATUS ACCORDING TO PRESENT EMBODIMENT (51) Int. Cl.
*H03K 17/687* (2006.01)
*H03K 17/06* (2006.01)
*H03K 17/082* (2006.01)

(52) U.S. Cl.
CPC ..... *H03K 17/0822* (2013.01); *H03K 17/6871* (2013.01); *H03K 17/6874* (2013.01); *H03K 2017/066* (2013.01); *H03K 2217/0009* (2013.01); *H03K 2217/0054* (2013.01)

(56) References Cited

U.S. PATENT DOCUMENTS

| | | | |
|---|---|---|---|
| 6,586,780 B1 * | 7/2003 | Terashima | H01L 27/0623 257/110 |
| 2002/0135415 A1 | 9/2002 | Dufort | |
| 2013/0187697 A1 * | 7/2013 | Choy | H03K 17/6872 327/298 |
| 2014/0049174 A1 * | 2/2014 | Radermacher | H05B 33/0821 315/200 R |

FOREIGN PATENT DOCUMENTS

| | | |
|---|---|---|
| JP | 07-046109 | 2/1995 |
| JP | 2004-531929 A2 | 10/2004 |
| JP | 2012-095168 A | 5/2012 |

OTHER PUBLICATIONS

Office Action issued Sep. 20, 2016 for corresponding Japanese Application No. 2013-196862.

* cited by examiner

FIG. 1

COMMENT: ESSENTIAL PART OF ULTRASOUND DIAGNOSTIC APPARATUS ACCORDING TO PRESENT EMBODIMENT

FIG.2

COMMENT: ENTIRETY OF HIGH BREAKDOWN VOLTAGE ANALOG SWITCH INTEGRATED CIRCUIT ACCORDING TO PRESENT EMBODIMENT

FIG. 3

COMMENT: HIGH BREAKDOWN VOLTAGE ANALOG SWITCH CIRCUIT ACCORDING TO PRESENT EMBODIMENT

FIG.4

COMMENT: FLOATING GATE CONTROL CIRCUIT AND OUTPUT SWITCH IN PRESENT EMBODIMENT

FIG. 5

COMMENT: ESSENTIAL PART OF ULTRASOUND DIAGNOSTIC APPARATUS ACCORDING TO COMPARATIVE EXAMPLE

FIG. 6

COMMENT: ENTIRETY OF HIGH BREAKDOWN VOLTAGE ANALOG SWITCH INTEGRATED CIRCUIT ACCORDING TO COMPARATIVE EXAMPLE

FIG. 7

COMMENT: PART OF HIGH BREAKDOWN VOLTAGE ANALOG SWITCH INTEGRATED CIRCUIT ACCORDING TO COMPARATIVE EXAMPLE

SEMICONDUCTOR SWITCH CIRCUIT, SIGNAL PROCESSING APPARATUS, AND ULTRASOUND DIAGNOSTIC APPARATUS

BACKGROUND OF THE INVENTION

1. Field of the Invention

The present invention relates to a semiconductor switch circuit equipped with a high breakdown voltage bidirectional analog switch, and a signal processing apparatus and an ultrasound diagnostic apparatus using the semiconductor switch circuit.

2. Description of the Related Art

There has recently been a demand for further miniaturization and decreasing in costs for an ultrasound diagnostic apparatus with its wider use. The ultrasound diagnostic apparatus has a piezoelectric probe for transmitting and receiving ultrasound, and a bidirectional analog switch for transmitting and receiving a drive signal of the piezoelectric probe and a signal of the ultrasound and further includes a plurality of power supplies for driving the bidirectional analog switch. A current ultrasound diagnostic apparatus is accompanied by a problem that the mounting of a plurality of power supplies becomes a bottleneck and a drastic size reduction cannot be realized.

There has been described in the problem of JP-2012-95168-A that "there is provided a semiconductor device of a bidirectional analog switch having satisfactory linearity and less reduced in power loss, and there is provided an ultrasound diagnostic apparatus high in detection precision". There has been described in its solving means that "there is provided a semiconductor device of a bidirectional analog switch incorporating a switch circuit capable of turning-on or off bidirectionally and a drive circuit for the switch circuit therein, wherein the drive circuit is connected to first and second power supplies, the first power supply voltage is greater than or equal to the maximum voltage value of a signal applied to an input/output terminal of the switch circuit, and the second power supply voltage is less than or equal to the minimum voltage value of the signal applied to the input/output terminal of the switch circuit, and further, wherein the drive circuit has zener diodes and P type MOSFETs connected in series between the first power supply and the switch circuit. There is provided an ultrasound diagnostic apparatus equipped with the semiconductor device".

Figure 5:
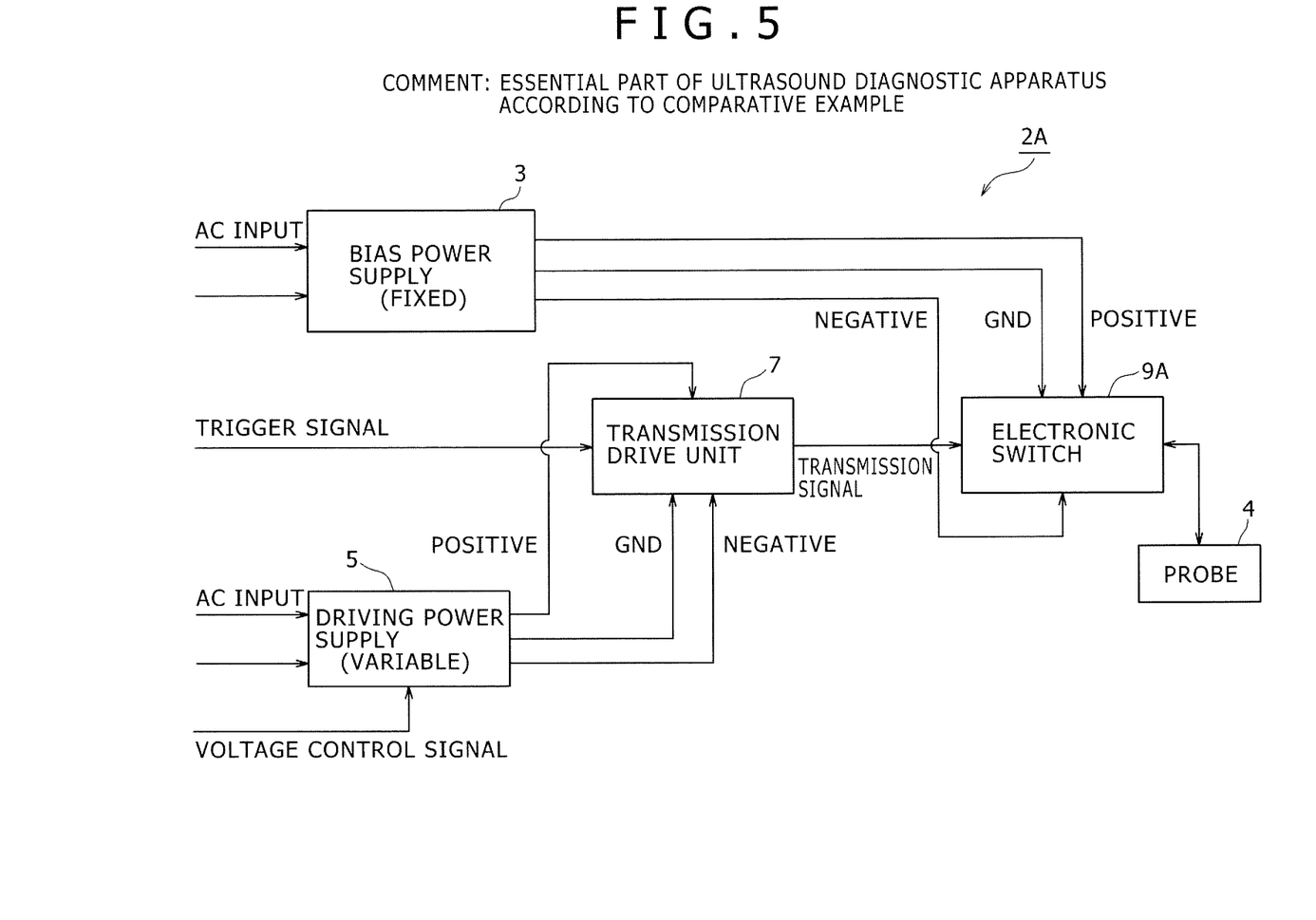
FIG. 5 is a block diagram illustrating an essential configuration of an ultrasound diagnostic apparatus according to a comparative example.

An essential configuration of an ultrasound diagnostic apparatus 2A according to a comparative example is shown in FIG. 5.

As shown in FIG. 5, the ultrasound diagnostic apparatus 2A has a transmission drive unit 7 that generates a transmission signal, based on a trigger signal, an electronic switch 9A that supplies the transmission signal to a probe 4, the probe 4 comprised of a plurality of piezoelectric elements (not shown), a driving power supply 5 that supplies a variable voltage, and a bias power supply 3 that supplies a fixed voltage. The ultrasound diagnostic apparatus 2A performs switching operations of a plurality of bidirectional analog switches lying inside the electronic switch 9A and supplies the transmission signal to the prescribed piezoelectric element of the probe 4 to thereby perform ultrasound scanning.

The electronic switch 9A has semiconductor switch circuits being the plural bidirectional analog switches in association with the plural piezoelectric elements provided in the probe 4. AS compared with a mechanical relay, the semiconductor switch circuit has various advantages such as high reliability, a reduction in size, high-speed switching, low power consumption, a noise reduction, a long lifetime, etc.

The driving power supply 5 generates positive and negative drive voltages, based on a voltage control signal in response to the supply of AC power (described as an AC input in the figure) and supplies the generated positive and negative drive voltages to the transmission drive unit 7.

The bias power supply 3 generates fixed positive and negative bias voltages in response to the supply of the AC power and supplies the generated positive and negative bias voltages to the electronic switch 9A. The positive and negative bias voltages are voltages higher than the positive and negative drive voltages supplied from the driving power supply 5.

Thus, the ultrasound diagnostic apparatus 2A has both the driving power supply 5 that uniquely generates the drive voltages necessary for the operation of the transmission drive unit 7, and the bias power supply 3 that uniquely generates the bias voltages necessary for the control of the electronic switch 9A. Consequently, the ultrasound diagnostic apparatus 2A has caused an increase in the number of components and an inhibition factor of miniaturization.

Figure 6:
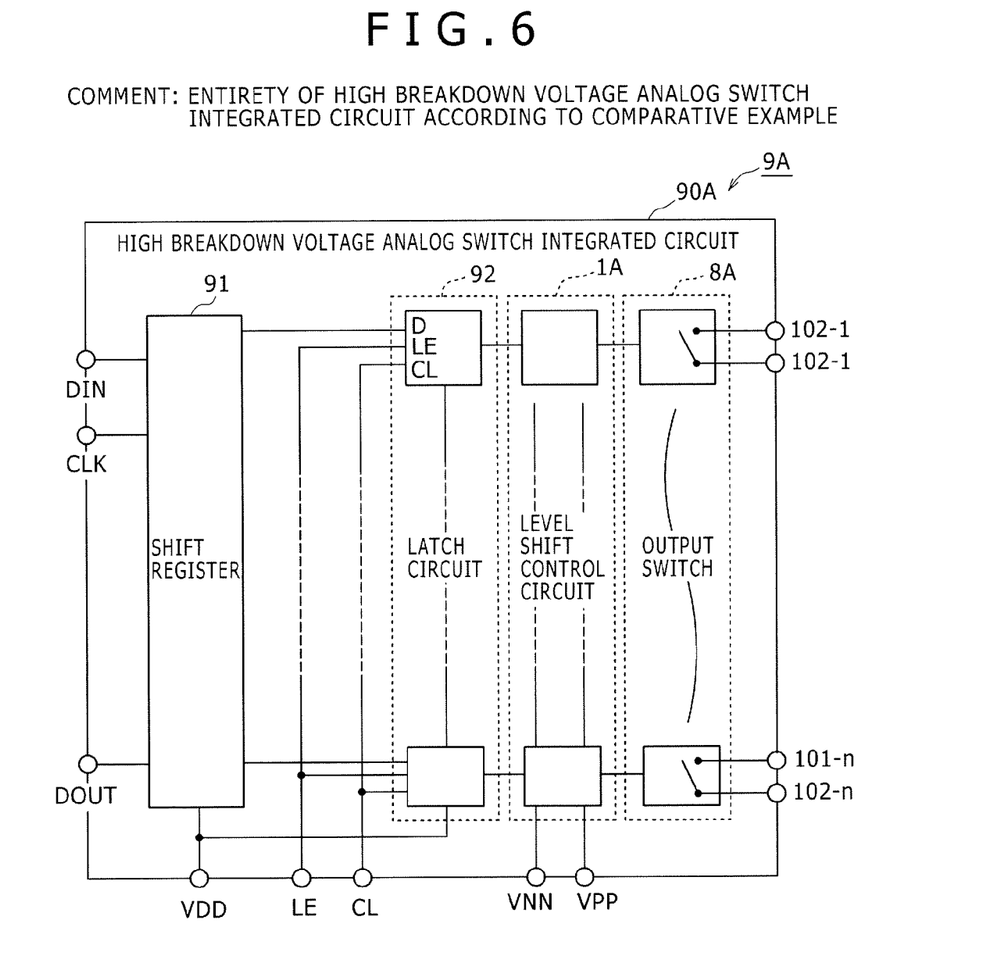
FIG. 6 is a block diagram showing the entirety of a high breakdown voltage analog switch integrated circuit according to a comparative example.

FIG. 6 shows a block diagram of a high breakdown voltage analog switch integrated circuit 90A according to a comparative example.

The high breakdown voltage analog switch integrated circuit 90A (one example of semiconductor switch circuits) according to the comparative example, which configures an electronic switch 9A, has a shift register 91 that performs operation switching of a plurality of switches, a latch circuit 92 that holds the operation states of the switches, an output switch 8A, and a level shift control circuit 1A that drives the output switch 8A.

The shift register 91 outputs an input signal DIN to each stage of the latch circuit 92 as a signal D while being shifted in synchronization with an input signal CLK. An output signal DOUT is outputted as a signal outputted to the last stage of the latch circuit 92.

The latch circuit 92 is configured in a multiple stage and latches the signal D and a signal CL therein in accordance with an input signal LE. The latch circuit 92 outputs the latched signals to respective stages of the level shift control circuit 1A.

The level shift control circuit 1A is configured in a multiple stage and turns ON/OFF respective stages of the output switch 8A, based on the signals latched by the latch circuit 92.

The output switch 8A is configured in a multiple stage. The first stage of the output switch 8A performs switching as to whether or not to transmit an analog voltage signal between an input/output terminal 101-1 and an input/output terminal 102-1. Subsequently, in the same manner as above, the n-th stage of the output switch 8A performs switching as to whether or not to transmit an analog voltage signal between an input/output terminal 101-$n$ and an input/output terminal 102-$n$.

The shift register 91 and the latch circuit 92 constitute a low voltage circuit with a low voltage power supply VDD as a drive power supply. The output switch 8A and the level shift control circuit 1A constitute a high voltage circuit with a positive high voltage power supply VPP and a negative high voltage power supply VNN as drive power supplies. The positive high voltage power supply VPP is set higher than the signal voltage applied to each of the input/output terminals 101 and 102. The negative high voltage power supply VNN is set lower than the signal voltage applied to each of the input/output terminals 101 and 102.

Figure 7:
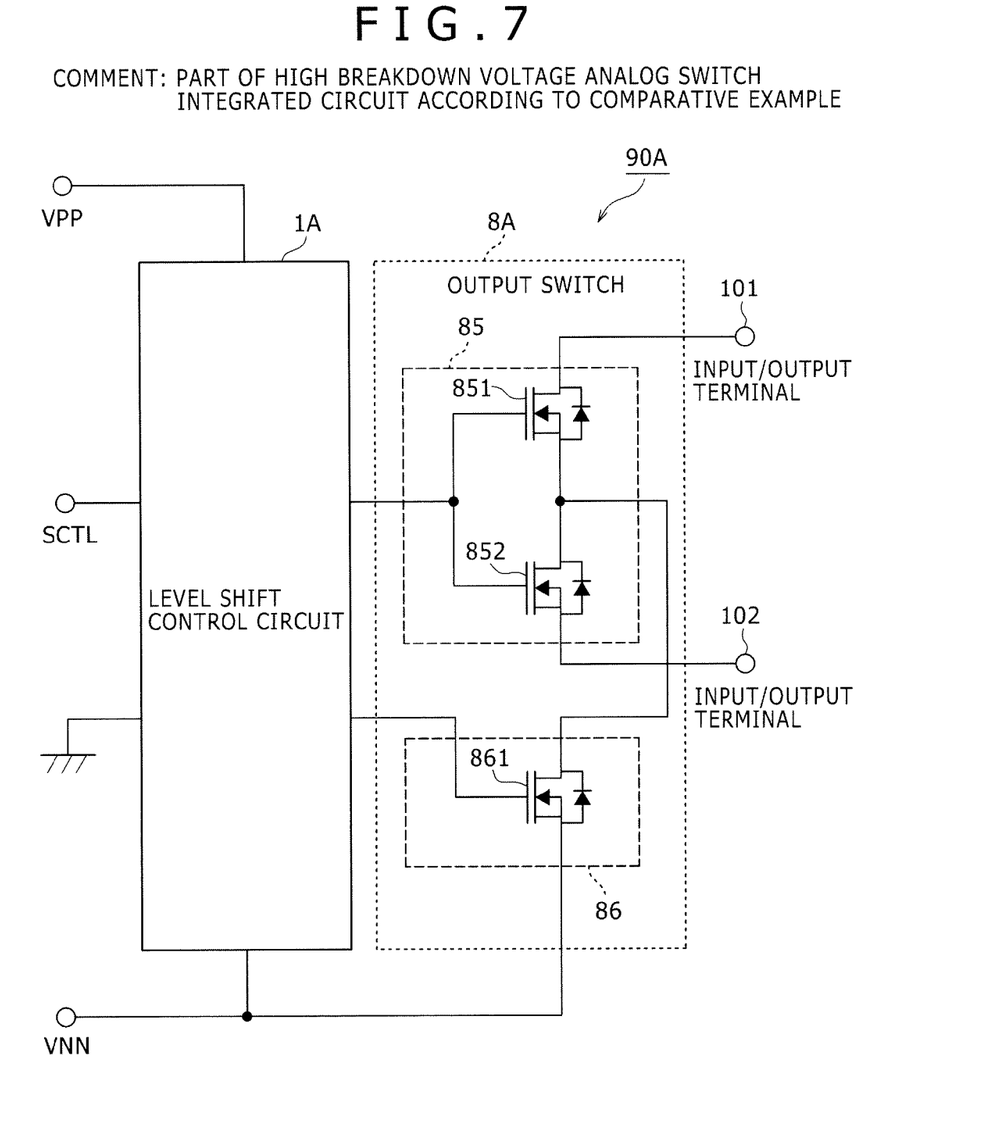
FIG. 7 is a diagram illustrating part of the high breakdown voltage analog switch integrated circuit according to the comparative example.

FIG. 7 shows a circuit diagram of part of the high breakdown voltage analog switch integrated circuit 90A according to the comparative example. FIG. 7 shows only one stage of the output switch 8A that serves as the essential part of the high breakdown voltage analog switch integrated circuit 90A, and the level shift control circuit 1A that serves as its drive circuit.

As shown in FIG. 7, the output switch 8A has a switch pair 85 comprised of two MOSFETs (Metal-Oxide-Semiconductor Field-Effect Transistors) 851 and 852 of which the gates and sources are each connected to one another, and a switch unit 86 comprised of a MOSFET 861.

The MOSFET 851 has a drain connected to the input/output terminal 101. The MOSFET 852 has a drain connected to the input/output terminal 102. The MOSFET 861 has a source connected to the negative high voltage power supply VNN and a drain connected to a connecting node of sources of the MOSFETs 851 and 852.

The level shift control circuit 1A supplied with the positive high voltage power supply VPP and the negative high voltage power supply VNN as drive power supplies controls the output switch 8A on the basis of a switch control signal SCTL.

The switch pair 85 is an analog switch that performs the transmission and cut off of a high voltage signal between the input/output terminal 101 and the input/output terminal 102. The switch unit 86 acts as a shunt for improving off isolation performance indicative of signal cut off performance when the analog switch is turned off.

When the high voltage signal is applied to the input/output terminals 101 and 102, a high voltage is applied between the gates and sources of the switch pair 85. Therefore, the MOSFETs 851 and 852 that configure the switch pair 85 need to have a gate structure of which is a high breakdown voltage. Since the MOSFETs 851 and 852 of which the gates have such a high breakdown voltage are high in on voltage, the level shift control circuit 1A that drives them also needs to be supplied with the high voltage power supply.

SUMMARY OF THE INVENTION

A high breakdown voltage analog switch integrated circuit is required to have a low insertion loss, high breakdown voltage performance capable of withstanding a high voltage signal having positive and negative polarities, and off isolation performance (impedance in an OFF state) relative to a high frequency signal. Therefore, the high breakdown voltage analog switch integrated circuit of the comparative example needs the bias power supply 3 (refer to FIG. 5) that supplies the positive high voltage power supply VPP and the negative high voltage power supply VNN and has led to an inhibition factor to a size reduction and a reduction in power consumption.

Consider where in FIG. 7 of the comparative example, the positive high voltage power supply VPP supplied to the level shift control circuit 1A which is a drive circuit of the analog switch is made low. Each of the MOSFETs 851 and 852 included in the switch pair 85 is not supplied with a sufficient on voltage due to an insertion loss and is in danger of losing a function as a switch in the worst case.

Further, when the negative high voltage power supply VNN is set to a low voltage or a ground potential, the impedance of a line between the input/output terminals 101 and 102 is reduced due to a parasitic diode of the MOSFET 851 of the switch pair 85 where a signal having a potential lower than the low voltage or the ground potential is applied to the input/output terminal 101. Likewise, when the signal having the potential lower than the negative high voltage power supply VNN is applied to the input/output terminal 102, the impedance of the line between the input/output terminals 101 and 102 is reduced due to a parasitic diode of the MOSFET 852 of the switch pair 85. It is not possible to maintain the off isolation performance of the switch pair 85 in any case.

It is therefore an object of the present invention to provide a high breakdown voltage semiconductor switch circuit capable of being controlled by a low voltage power supply.

In order to achieve the above object, the invention of a semiconductor switch circuit in the inventions has a first switch pair comprised of two MOSFETs having gates connected to one another and sources connected to one another, and a zener diode reversely connected between the gates and sources of the MOSFETs; a second switch pair comprised of two MOSFETs having gates connected to one another and sources connected to one another, and a zener diode reversely connected between the gates and sources of the MOSFETs; and a third switch pair comprised of two MOSFETs having gates connected to one another and sources connected to one another. The first switch pair and the second switch pair are connected in series between two input/output terminals through a connecting node. The third switch pair is connected to the connecting node between the first switch pair and the second switch pair.

Thus, the semiconductor switch circuit does not need a positive or negative high voltage power supply which has been essential to its own driving and maintenance of the off isolation performance and is capable of controlling a high voltage signal with positive and negative polarities by only a low voltage power supply.

The invention of a signal processing apparatus includes a semiconductor switch circuit according to the present invention.

Thus, since the signal processing apparatus does not need the positive or negative high voltage power supply which has been essential to the driving of the semiconductor switch circuit and the maintenance of the off isolation performance, its miniaturization and cost reduction are enabled. Reducing the high voltage circuit which has been required for the control of the electronic switch makes it easy to design a circuit board with its reduction and decreases a failure probability with a decrease in the number of components, thereby enhancing reliability of the signal processing apparatus.

The invention of an ultrasound diagnostic apparatus includes a semiconductor switch circuit according to the present invention, and a piezoelectric probe to which the semiconductor switch circuit is connected.

Thus, since the ultrasound diagnostic apparatus does not need the positive or negative high voltage power supply which has been essential to the driving of the semiconductor switch circuit and the maintenance of the off isolation performance, its miniaturization and cost reduction are enabled. Reducing the high voltage circuit which has been required for control of the electronic switch makes it easy to design a substrate with its reduction and decreases a failure probability with a decrease in the number of components, thereby enhancing reliability of the ultrasound diagnostic apparatus.

Other means will be described in the modes for carrying out the invention.

According to the present invention, it is possible to provide a high breakdown voltage semiconductor switch circuit capable of being controlled by a low voltage power supply.

BRIEF DESCRIPTION OF THE DRAWINGS

Other objects and advantages of the invention will become apparent from the following description of embodiments with reference to the accompanying drawings in which.

DESCRIPTION OF THE PREFERRED EMBODIMENTS

Modes for carrying out the present invention will hereinafter be described in detail with reference to the accompanying drawings.

First Embodiment

Figure 1:
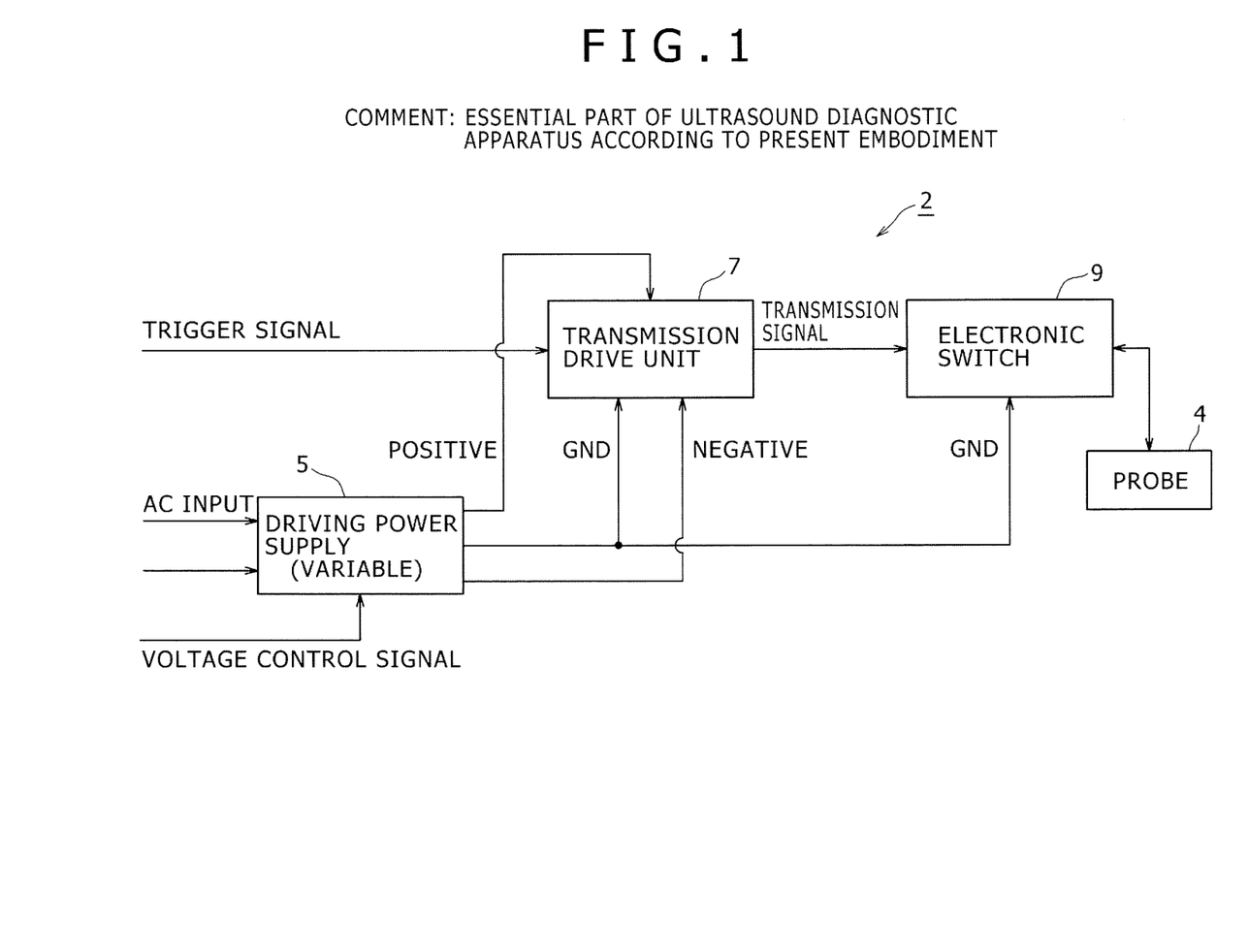
FIG. 1 is a block diagram illustrating an essential configuration of an ultrasound diagnostic apparatus according to the present embodiment.

FIG. 1 is a configuration diagram showing an essential part of an ultrasound diagnostic apparatus 2 according to the present embodiment.

As shown in FIG. 1, the ultrasound diagnostic apparatus 2 of the present embodiment has a transmission drive unit 7 that generates a transmission signal based on a trigger signal, an electronic switch 9 that supplies the transmission signal to a probe 4, the probe 4 provided with a plurality of piezoelectric elements (not shown), and a driving power supply 5 that supplies a variable voltage.

The electronic switch 9 is comprised of a semiconductor switch circuit. The electronic switch 9 in the present embodiment needs not to have the bias power supply 3 (refer to FIG. 5) which has been essential to the comparative example. Therefore, the application of a high breakdown voltage analog switch integrated circuit 90 of the present embodiment to the electronic switch 9 makes it unnecessary to provide the bias power supply 3 which has been essential to the ultrasound diagnostic apparatus 2A of the comparative example. Thus, the ultrasound diagnostic apparatus 2 of the present embodiment is simpler in configuration than the ultrasound diagnostic apparatus 2A of the comparative example and can be miniaturized and reduced in cost.

Further, circuit board design is made easy by reducing circuit's high voltage parts. Reducing the number of component parts reduces a failure rate and improves the reliability of the ultrasound diagnostic apparatus 2.

Incidentally, the semiconductor switch circuit of the present embodiment is not limited to the application to the ultrasound diagnostic apparatus 2, but may be applied to an arbitrary signal processing apparatus that processes an analog signal.

Figure 2:
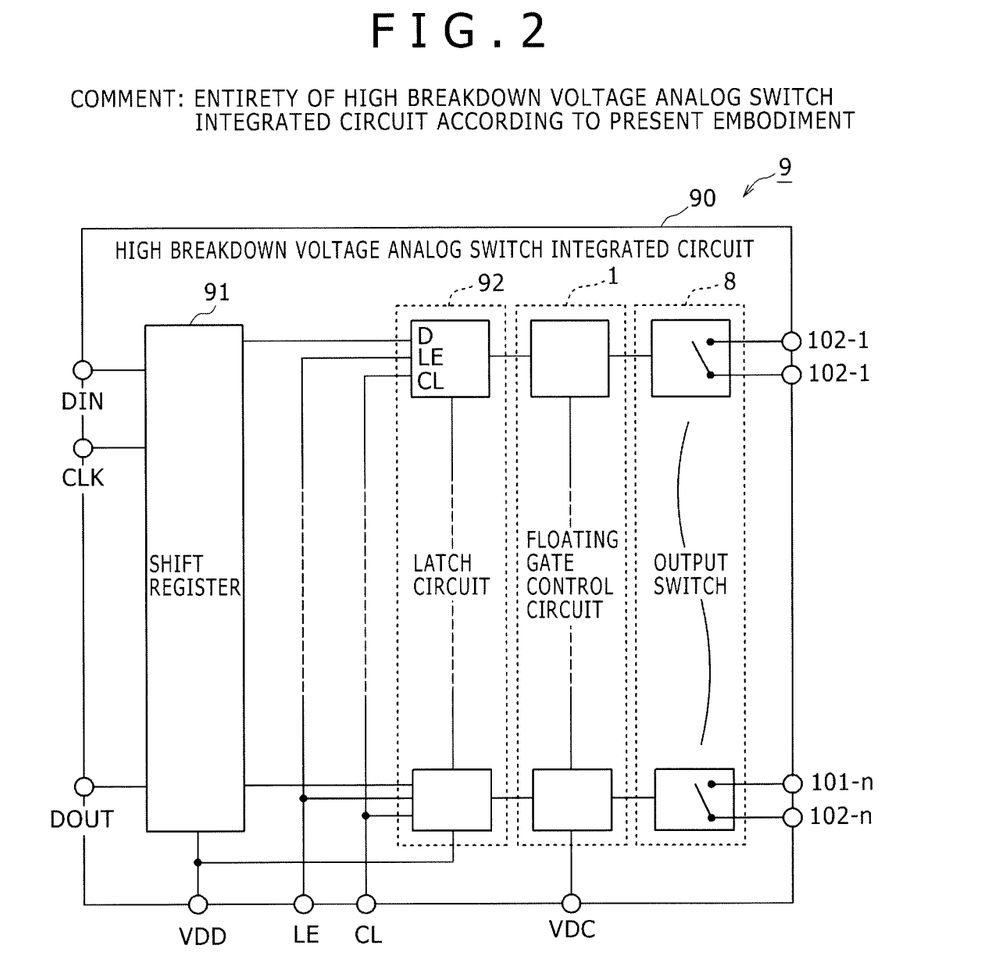
FIG. 2 is a block diagram showing the entirety of a high breakdown voltage analog switch integrated circuit according to the present embodiment.

FIG. 2 is a block diagram showing the entirety of the high breakdown voltage analog switch integrated circuit 90 according to the present embodiment.

As shown in FIG. 2, the high breakdown voltage analog switch integrated circuit 90 (one example of semiconductor switch circuit) that configures the electronic switch 9 of the present embodiment is arranged such that in the high breakdown voltage analog switch integrated circuit 90A (refer to FIG. 6) of the comparative example, the level shift control circuit 1A is replaced with a floating gate control circuit 1 and the output switch 8A is replaced with an output switch 8. Further, the positive high voltage power supply VPP and the negative high voltage power supply VNN supplied in the comparative example are not supplied but low voltage power supplies VDC and VDD are supplied. Here, the voltage of the low voltage power supply VDC may be set lower than the maximum value of a signal voltage applied to input/output terminals 101 and 102.

The high breakdown voltage analog switch integrated circuit 90 of the present embodiment is intensively incorporated with output switches 8 configured in a multistage form. Thus, the high breakdown voltage analog switch integrated circuit 90 can be connected to an array of the piezoelectric elements of the piezoelectric probe 4.

The high breakdown voltage analog switch integrated circuit 90 can be controlled by the same input signals DIN, CLK, LE and CL as those employed in the high breakdown voltage analog switch integrated circuit 90A of the comparative example. It is thus possible to use it by being connected to the same interface as that in the comparative example. That is, when the high breakdown voltage analog switch integrated circuit 90 of the present embodiment is used, the ultrasound diagnostic apparatus 2 is capable of connecting a similar input/output signal interface as in the case with the high breakdown voltage analog switch integrated circuit 90A of the comparative example and performing control similar to the comparative example. Therefore, the high breakdown voltage analog switch integrated circuit 90 of the present embodiment enables easy substitution of the high breakdown voltage analog switch integrated circuit 90A of the comparative example.

Figure 3:
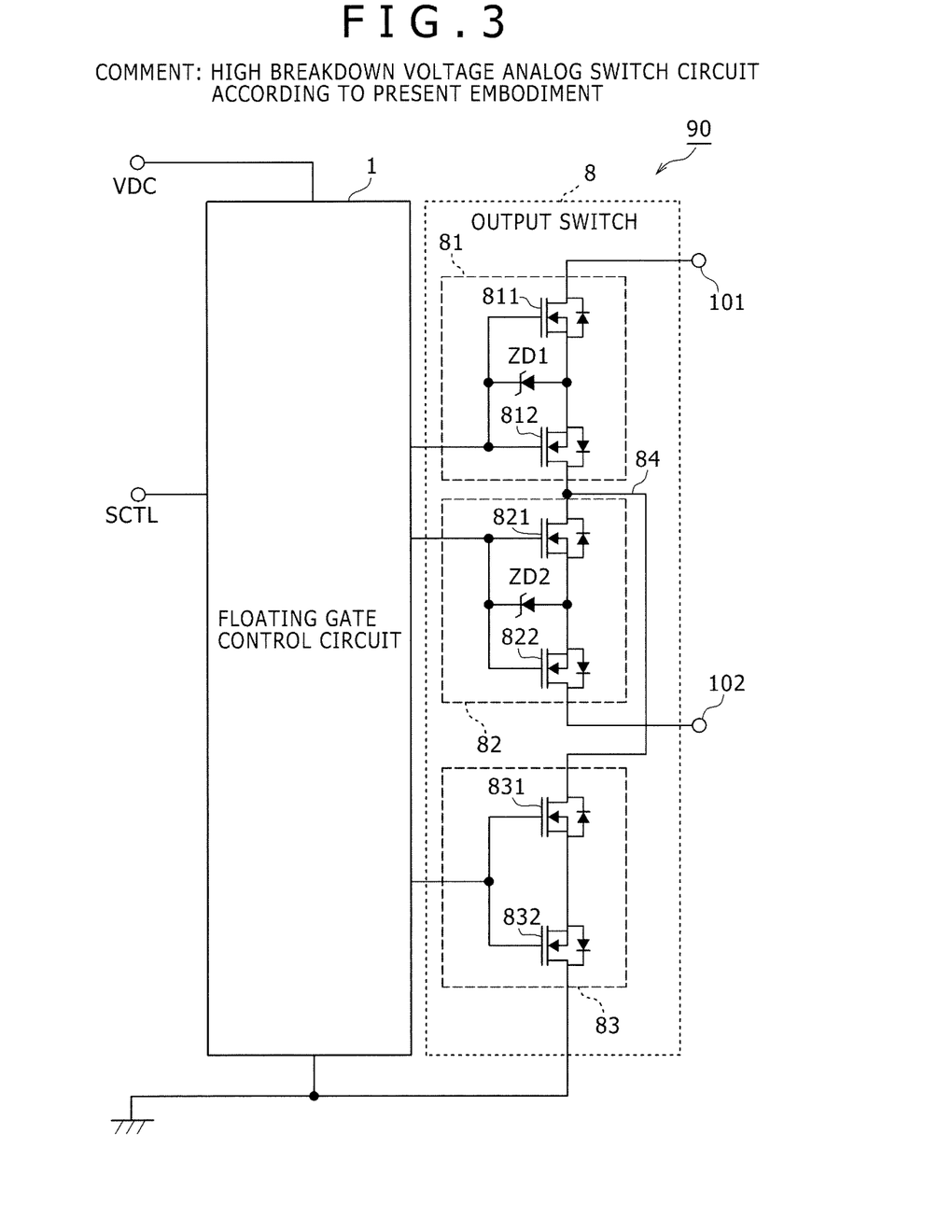
FIG. 3 is a diagram depicting part of the high breakdown voltage analog switch integrated circuit according to the present embodiment.

FIG. 3 is a diagram showing part of the high breakdown voltage analog switch integrated circuit 90 according to the present embodiment.

As shown in FIG. 3, the high breakdown voltage analog switch integrated circuit 90 includes the floating gate control circuit 1 and the output switch 8. In FIG. 3, the floating gate control circuit 1 and the output switch 8 are shown by only one stage.

The output switch 8 includes a first switch pair 81, a second switch pair 82, and a third switch pair 83 and is connected with the input/output terminals 101 and 102.

The first switch pair 81 is comprised of two MOSFETs 811 and 812 of which the gates and sources are each connected to one another, and a zener diode ZD1 connected to a gate-to-drain in each MOSFET in the reverse direction.

Likewise, the second switch pair 82 is comprised of two MOSFETs 821 and 822 of which the gates and sources are each connected to one another, and a zener diode ZD2 connected to a gate-to-source in each MOSFET in the reverse direction. The first switch pair 81 and the second switch pair 82 are connected in series between the two input/output terminals 101 and 102. The first switch pair 81 and the second switch pair 82 are connected to each other by a connecting node 84. A drain of the MOSFET 811 of the first switch pair 81 is connected to the input/output terminal 101. A drain of the MOSFET 822 of the second switch pair 82 is connected to the input/output terminal 102.

The third switch pair 83 is comprised of two MOSFETs 831 and 832 of which the gates and sources are each connected to one another. A drain of the MOSFET 831 is connected to the connecting node 84 of the first switch pair 81 and the second switch pair 82. A drain of the MOSFET 832 is connected to the ground.

The floating gate control circuit 1 controls the first switch pair 81, the second switch pair 82 and the third switch pair 83 included in the output switch 8. The floating gate control circuit 1 is supplied with the low voltage power supply VDC and inputted with a switch control signal SCTL from each stage of a latch circuit 92 (refer to FIG. 2). The switch control signal SCTL is a signal for switching the transmission and cutoff of each signal of the output switch 8. When the switch control signal SCTL is at an H level, the output switch 8 transmits a signal between the input/output terminals 101 and 102. When the switch control signal SCTL is at an L level, the output switch 8 cuts off between the input/output terminals 101 and 102.

The MOSFETs 811, 812, 821, 822, 831, and 832 that configure the first switch pair 81, the second switch pair 82 and the third switch pair 83 of the output switch 8 are high breakdown voltage N channel MOSFETs and have element breakdown voltages not less than the signal voltage of each of the input/output terminals 101 and 102. The MOSFETs used in the output switch 8 in the present embodiment adopt elements relatively low in gate oxide film breakdown voltage and thus low in on voltage, rather than such high breakdown voltage MOSFETs as used in the output switch 8A (refer to FIG. 7) in the comparative example.

The MOSFETs 811, 812, 821 and 822 are made equal to each other in terms of a structure related to device current performance such as a channel width. Thus, the output switch 8 is capable of ensuring symmetry of signal transmission between the input/output terminals 101 and 102 in its ON state. The reason why this effect is obtained will be described below.

A high voltage signal having positive and negative polarities is applied to the high breakdown voltage analog switch integrated circuit 90 used in the electronic switch 9 of the ultrasound diagnostic apparatus 2. It is extremely important to transmit the high voltage signal having the positive and negative polarities while maintaining the symmetry with both polarities when the corresponding analog switch is in an ON state.

The performance of the analog switch is determined by the impedance between its input/output terminals. The impedance between the input/output terminals of the analog switch is made up of a combination of ON resistances of the respective MOSFETs existing between the input/output terminals and impedances due to parasitic diodes of the respective MOSFETs.

The MOSFETs 811 and 812, and the MOSFETs 821 and 822 exist in a route from the input/output terminal 101 to the input/output terminal 102 connected to the output switch 8. The impedance from the input/output terminal 101 to the input/output terminal 102 is made up of a combination of an ON resistance of the MOSFET 811, an impedance due to a parasitic diode of the MOSFET 812, an ON resistance of the MOSFET 821, and an impedance due to a parasitic diode of the MOSFET 822.

The impedance from the input/output terminal 102 to the input/output terminal 101 is made up of a combination of an ON resistance of the MOSFET 822, an impedance due to a parasitic diode of the MOSFET 821, an ON resistance of the MOSFET 812, and an impedance due to a parasitic diode of the MOSFET 811. Thus, the impedance of the transmission route between the input/output terminals 101 and 102 varies depending on the direction and polarity of the signal between the input/output terminals 101 and 102.

In the present embodiment, the MOSFETs 811 and 812 included in the first switch pair 81, and the MOSFETs 821 and 822 included in the second switch pair 82 are all equal to each other in current performance. Here, the current performance of each MOSFET indicates, for example, an impedance due to an ON resistance and a parasitic diode. Thus, since the combined impedances can be made identical to each other at both positive and negative polarities, the high breakdown voltage analog switch integrated circuit 90 is capable of transmitting the high voltage signal having the positive and negative polarities between the input/output terminals 101 and 102 while maintaining the symmetry with both polarities when the output switch 8 is in the ON state.

A description will next be made about the switching operation of the high breakdown voltage analog switch integrated circuit 90 of the present embodiment. In the high breakdown voltage analog switch integrated circuit 90, the first switch pair 81, the second switch pair 82 and the third switch pair 83 are operated as bidirectional analog switches by performing charging/discharging on their own gate-source capacitances to change the impedance between their drain terminals. That is, the MOSFETs 811 and 812 are turned on by charging the gate-source capacitances of the MOSFETs 811 and 812 that configure the first switch pair 81. Consequently, the first switch pair 81 is turned on. The gate-source capacitances of the MOSFETs 811 and 812 are discharged to thereby turn off the MOSFETs 811 and 812, so that the switch element is also brought to an OFF state. The second switch pair 82 and the third switch pair 83 are also operated in a manner similar to the first switch pair 81.

In the high breakdown voltage analog switch integrated circuit 90, the combination of the first switch pair 81 and the second switch pair 82 directly connected between the input/output terminals 101 and 102 functions as a bidirectional analog switch which performs the transmission or cut-off of a signal applied to each of the input/output terminals 101 and 102. The third switch pair 83 functions as a shunt switch for improving isolation performance. The isolation performance is signal cut off performance between the two input/output terminals 101 and 102 at the turning off of the analog switch and is represented by the impedance at the turning off.

The first switch pair 81 and the second switch pair 82 are both turned on simultaneously or both turned off simultaneously. In contrast, the third switch pair 83 is turned on and off reversely to the first switch pair 81 and the second switch pair 82. That is, when the first switch pair 81 and the second switch pair 82 are on, the third switch pair 83 is turned off. When the first switch pair 81 and the second switch pair 82 are off, the third switch pair 83 is turned on.

The first switch pair 81, the second switch pair 82 and the third switch pair 83 are controlled by the floating gate control circuit 1 on the basis of the switch control signal SCTL. The floating gate control circuit 1 serves to charge or discharge an electrical charge from or into the gate-source capacitance of each MOSFET that configures each switch pair. The floating gate control circuit 1 controls ON/OFF of the first switch pair 81, the second switch pair 82 and the third switch pair 83, based on the switch control signal SCTL inputted thereto.

For example, when the switch control signal SCTL is at an H level, the floating gate control circuit 1 turns on the first switch pair 81 and the second switch pair 82 and turns off the third switch pair 83.

When the switch control signal SCTL is at an L level, the floating gate control circuit 1 turns off the first switch pair 81 and the second switch pair 82 and turns on the third switch pair 83.

When the switch control signal SCTL is set to the H level, the gate-source capacitances of the first switch pair 81 and the second switch pair 82 are charged from the low voltage power supply VDC by the floating gate control circuit 1, so that the first switch pair 81 and the second switch pair 82 are brought to an ON state to reach a low impedance between the input/output terminals 101 and 102, whereby a signal is transmitted. At this time, the third switch pair 83 is turned off because the gate-source capacitance of the third switch pair 83 that performs a logical operation opposite to the first switch pair 81 and the second switch pair 82 is discharged to the ground.

When the switch control signal SCTL is set to the L level contrary to this, the electrical charges accumulated in the gate-source capacitances of the first switch pair 81 and the second switch pair 82 are discharged to the ground by the floating gate control circuit 1, so that the first switch pair 81 and the second switch pair 82 are brought to an OFF state to reach a high impedance between the input/output terminals 101 and 102, whereby a signal is cut off. At this time, the gate-source capacitance of the third switch pair 83 that performs a logical operation opposite to the first switch pair 81 and the second switch pair 82 is charged from the low voltage power supply VDC so that the third switch pair 83 is turned on.

When a positive high voltage signal is applied to the input/output terminal 101 or the input/output terminal 102, the common source for each switch pair is in a floating state, with each switch pair being in an ON state. Therefore, the potential of the source has the potential of the high voltage signal. Therefore, if the potential of the gate of each switch pair is set as a fixed potential, a high voltage is applied between the gate and source of each switch pair, thus causing a gate oxide film breakdown if left. In order to avoid it, the floating gate control circuit 1 of the present embodiment controls a gate voltage of each switch pair.

When each switch pair is ON/OFF-controlled, the floating gate control circuit 1 performs control to hold a prescribed electrical charge accumulated in the gate-source capacitance and hold a prescribed gate-source voltage. At this time, the floating gate control circuit 1 allows the gate voltage of each switch pair to follow the potential of its source.

When each switch pair is turned on, the floating gate control circuit 1 controls the gate-source voltage of the switch pair to be held at a voltage given by the low voltage power supply VCD. When each switch pair is turned off, the floating gate control circuit 1 controls the gate-source voltage of the switch pair to be held at a voltage less than the threshold of each MOSFET that configures the switch pair.

On the other hand, when a negative high voltage signal is applied to the input/output terminal 101 or the input/output terminal 102, a node to which the sources of the MOSFETs 811 and 812 are connected might become the potential of the negative high voltage signal due to the current flowing through the parasitic diode of the MOSFET 811 or 812 that configures the first switch pair 81. In order to avoid it, the zener diode ZD1 is reversely connected between the gates and sources of the MOSFETs 811 and 812. The zener diode ZD1 in the present embodiment uses a zener voltage of not less than the voltage of the low voltage power supply VDC and not greater than the gate oxide film breakdown voltage of each of the MOSFETs 811 and 812.

At this time, the second switch pair 82 placed in the same ON/OFF setting as the first switch pair 81 is similar to the above. A node to which the sources of the MOSFETs 821 and 822 are connected might become the potential of the negative high voltage signal due to the current flowing through the parasitic diode of the MOSFET 821 or 822 that configures the second switch pair 82. In order to avoid it, the zener diode ZD2 is reversely connected between the gates and sources of the MOSFETs 821 and 822. The zener diode ZD2 in the present embodiment uses a zener voltage of not less than the voltage of the low voltage power supply VDC and not greater than the gate oxide film breakdown voltage of each of the MOSFETs 821 and 822.

When the analog switch is in an ON state and the negative high voltage signal is applied to the input/output terminal 101 or 102, the current flows from the low voltage power supply VDC via the floating gate control circuit 1 and the zener diode ZD1 in the first switch pair 81 to hold the zener potential of the zener diode ZD1 between the gates and sources of the MOSFETs 821 and 822.

Likewise, in the case of the second switch pair 82 held in the ON state, the current flows from the low voltage power supply VDC via the floating gate control circuit 1 and the zener diode ZD2 to hold the zener potential of the zener diode ZD2 between the gates and sources of the MOSFETs 821 and 822.

Thus, the high breakdown voltage analog switch integrated circuit 90 which can be controlled by only the low voltage power supply VDC, is realized, and the driving with low power consumption is enabled compared with the control by the high voltage power supply such as in the comparative example.

The high breakdown voltage analog switch integrated circuit 90A (refer to FIG. 7) of the comparative example has a feature that it is configured by the MOSFETs each having the high breakdown voltage gate structure, and the on voltages of these MOSFETs are relatively high. Since the switch pair 85 in the comparative example is a so-called source follower circuit, the signal voltage applied to each of the input/output terminals 101 and 102 becomes high. When the gate-source voltage of the switch pair 85 in the comparative example falls below the on voltage of the switch element, each MOSFET cannot be turned on sufficiently, and the impedance between the input/output terminals 101 and 102 increases, thereby significantly degrading the signal transmission performance as the analog switch.

On the other hand, the high breakdown voltage analog switch integrated circuit 90 (refer to FIG. 3) of the present embodiment is driven by being supplied with only the low voltage power supply VDC. As each MOSFET that configures the output switch 8, an element having a general gate structure relatively low in breakdown voltage, rather than the high breakdown voltage gate structure such as described in the comparative example can be used, and the on voltage of each switch can be lowered. That is, the high breakdown voltage analog switch integrated circuit 90 of the present embodiment is an analog switch which is less reduced in attenuation from a region low in signal voltage to its high region and is excellent in linearity.

(Off Isolation Performance)

As another important characteristic of the analog switch, there is off isolation performance (impedance at the time of off) being cut off performance of input/output signals at the time of switch-off. When the analog switch is OFF, the impedance between the drain and source of each MOSFET configuring the analog switch becomes extremely high to interrupt between the input/output terminals. However, when the frequency of the signal applied to the input/output terminals become high, it is not possible to neglect the influence of the parasitic capacity of each MOSFET that configures the switch element, thus degrading the off isolation performance. At this time, the analog switch is not capable of sufficiently shutting off between the input/output terminals.

As effective means for solving this problem, there is a method for forming the analog switch in a T switch configuration. The output switch 8A (see FIG. 7) of the comparative example is a so-called T switch configuration in which the connecting node of the MOSFETs 851 and 852 is grounded by the shunt MOSFET 861. The T switch configuration is effective in improving the off isolation performance of the analog switch. The output switch 8A of the comparative example does not exert an effect at all if the shunt MOSFET 861 is not grounded to a potential lower than the signal voltage.

In the output switch 8A of the comparative example, the negative high voltage power supply VNN has been connected to the shut MOSFET 861. It was possible to maintain high off isolation performance unless the negative high voltage signal lower in potential than that of the negative high voltage power supply VNN is applied to the input/output terminals 101 and 102. However, if the negative high voltage signal lower in potential than the potential of the negative high voltage power supply VNN is applied to the input/output terminal 101 in the output switch 8A of the comparative example, the current flows through the input/output terminal 101 from the negative high voltage power supply VNN through the parasitic diode of the MOSFET 861 and the parasitic diode of the MOSFET 851. Similarly in the case where the negative high voltage signal lower in potential than the potential of the negative high voltage power supply VNN is applied to the input/output terminal 102, the current flows through the input/output terminal 102 from the negative high voltage power supply VNN. Therefore, the output switch 8A will rather cause degradation of the off isolation performance due to the shunt MOSFET 861.

The output switch 8 (refer to FIG. 3) of the present embodiment also has a T switch configuration in which the connecting node 84 of the first switch pair 81 and the second switch pair 82 is grounded by means of the shunt third switch pair 83. The output switch 8 is configured to connect the shunt third switch pair 83 to the ground, but is capable of maintaining the off isolation performance.

In the output switch 8 of the present embodiment, the high voltage signal is not grounded by the shunt element as it is. The output switch 8 isolates by the shunt third switch pair 83, a signal that leaks via the impedance of the first switch pair 81 or the second switch pair 82 at the turning off of the output switch 8. When the negative high voltage signal is applied to either of the input/output terminals 101 and 102, the output switch 8 further cuts off the reverse current from the ground to the signal source due to the parasitic diode of the MOSFET by means of the MOSFET held in the OFF state.

For example, if the positive high voltage signal is applied to the input/output terminal 101 when the output switch 8 is OFF, the MOSFET 811 cuts off the signal. If the negative high voltage signal is applied to the input/output terminal 102, the MOSFET 821 cuts off the signal.

When the output switch 8 itself is OFF, the output switch 8 turns off the first switch pair 81 and the second switch pair 82 and turns on the third switch pair 83. At this time, the third switch pair 83 short-circuits the connecting node 84 to the ground, and the impedance between the input/output terminals 101 and 102 is increased via the turned-off first switch pair 81 and second switch pair 82. Consequently, the output switch 8 reduces the leakage of the signal between the input/output terminal 101 and the input/output terminal 102. Thus, the output switch 8 is capable of exerting high off isolation performance in a wide signal voltage region from a minute signal having positive and negative polarities to a high voltage signal.

The switch circuits in the present embodiment are arranged symmetrically as also seen from either of the two input/output terminals 101 and 102. Similar output characteristics can be obtained even when either of the two input/output terminals 101 and 102 is selected as the input terminal. This can be said for the off isolation performance.

The ultrasound diagnostic apparatus 2 treats a transmission signal applied to the input terminal of the analog switch, and a received signal returned from the piezoelectric element. By using the high breakdown voltage analog switch integrated circuit 90 of the present embodiment in the electronic switch 9 of the ultrasound diagnostic apparatus 2, both transmitting and receiving signals can be isolated symmetrically.

Figure 4:
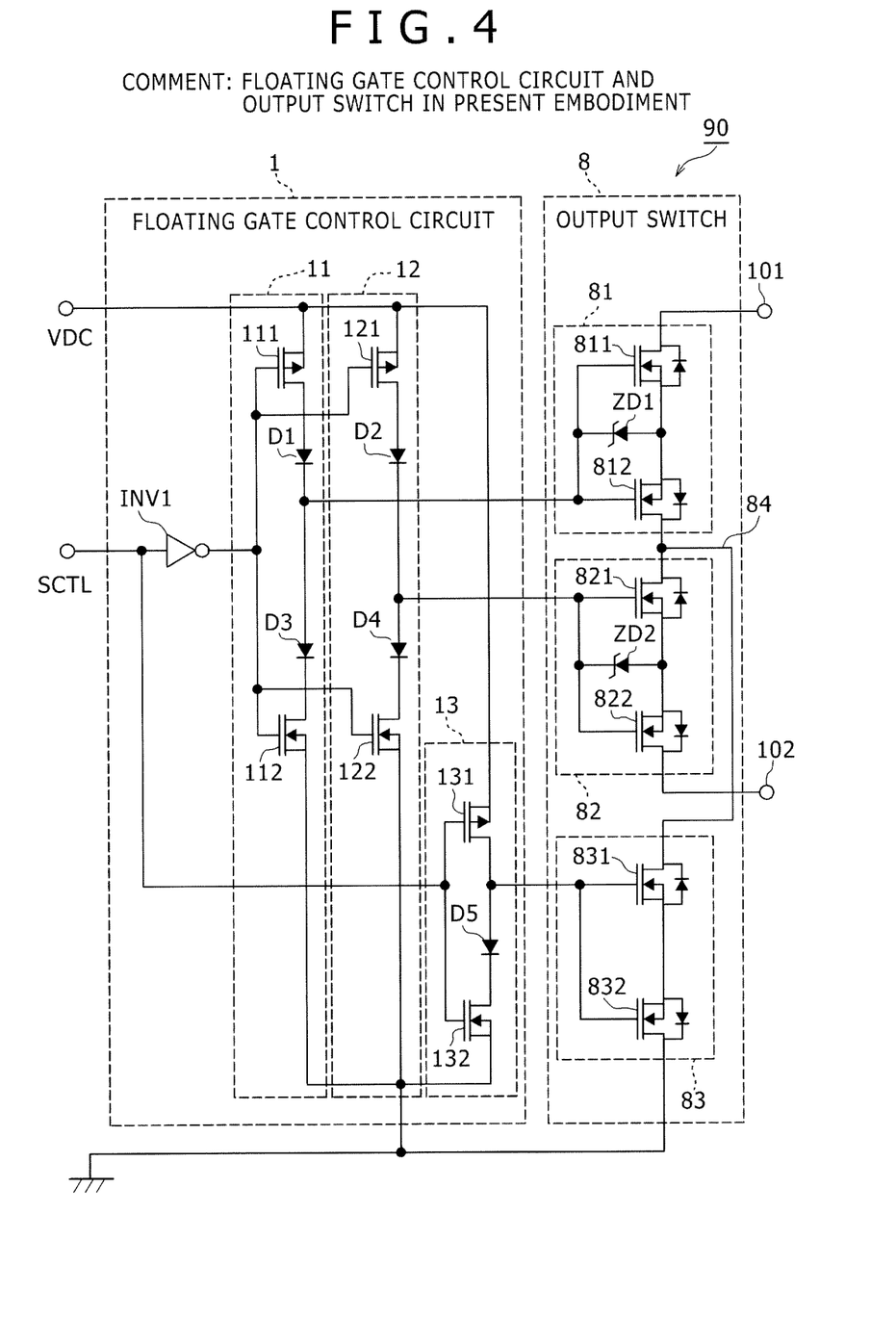
FIG. 4 is a circuit diagram showing a floating gate control circuit and an output switch according to the present embodiment.

FIG. 4 is a circuit diagram showing the floating gate control circuit 1 and the output switch 8 in the present embodiment. FIG. 4 shows an example of a circuit configuration considered to obtain the function of the internal configuration of the floating gate control circuit 1 in the present embodiment.

As shown in FIG. 4, the floating gate control circuit 1 includes a drive circuit 11 for the first switch pair 81, a drive circuit 12 for the second switch pair 82, a drive circuit 13 for the third switch pair 83, and an inverter INV1 which inverts the switch control signal SCTL and outputs its inverted signal.

The drive circuit 11 includes a high breakdown voltage P channel MOSFET 111 for charging the gates of the first switch pair 81 from the low voltage power supply VDC, a high breakdown voltage N channel MOSFET 112 for performing discharging from the gates of the first switch pair 81 to the ground, and high breakdown voltage diodes D1 and D3. The output side of the inverter INV1 is connected to a node to which a gate of the MOSFET 111 and a gate of the MOSFET 112 are connected. The reverse-current preventing high breakdown voltage diodes D1 and D3 are serially connected in the forward direction between a drain of the MOSFET 111 and a drain of the MOSFET 112. A connecting node of a cathode of the high breakdown voltage diode D1 and an anode of the high breakdown voltage diode D3 is connected to the gates of the first switch pair 81.

As with the drive circuit 11, the drive circuit 12 includes a high breakdown voltage P channel MOSFET 121 for charging the gates of the second switch pair 82 from the low voltage power supply VDC, a high breakdown voltage N channel MOSFET 122 for performing discharging from the gates of the second switch pair 82 to the ground, and high breakdown voltage diodes D2 and D4. The output side of the inverter INV1 is connected to a node to which a gate of the MOSFET 121 and a gate of the MOSFET 122 are connected. The reverse-current preventing high breakdown voltage diodes D2 and D4 are serially connected in the forward direction between a drain of the MOSFET 121 and a drain of the MOSFET 122. A connecting node of a cathode of the high breakdown voltage diode D2 and an anode of the high breakdown voltage diode D4 is connected to the gates of the second switch pair 82.

The drive circuit 13 includes a high breakdown voltage P channel MOSFET 131 for charging the gates of the third switch pair 83 from the low voltage power supply VDC, an N channel MOSFET 132 for performing discharging from the gates of the third switch pair 83 to the ground, and a high breakdown voltage diode D5. The switch control signal is inputted to a node to which a gate of the MOSFET 131 and a gate of the MOSFET 132 are connected. The reverse-current preventing high breakdown voltage diode D5 is connected in the forward direction between a drain of the MOSFET 131 and a drain of the MOSFET 132. A connecting node of the drain of the MOSFET 131 and an anode of the high breakdown voltage diode D5 is connected to the gates of the third switch pair 83.

A description will next be made about the mechanism of charging or discharging of an electrical charge into or from the gate-source capacitance of each switch element using the element units that configure the floating gate control circuit 1.

First, a description will be made of the case where the switch control signal SCTL is at an H level. At this time, a voltage approximately equal to the low voltage power supply VDC is applied to the switch control signal SCTL. The output of the inverter INV1 becomes an L level and reaches a voltage approximately equal to the ground.

Since no voltage is applied between the gate and source of the P channel MOSFET 131 of the drive circuit 13, the floating gate control circuit 1 is brought to an OFF state. Since the voltage is applied between the gate and source of the N channel MOSFET 132, the floating gate control circuit 1 is brought to an ON state. The third switch pair 83 is brought to an OFF state by discharging its own gate-source capacitance to the ground.

Since the voltage is applied between the gates and sources of the P channel MOSFETs 111 and 121 of the drive circuits 11 and 12, the floating gate control circuit 1 is brought to the ON state. Since no voltage is applied between the gates and sources of the N channel MOSFETs 112 and 122, the floating gate control circuit 1 is brought to the OFF state. The gate-source capacitances of the first switch pair 81 and the second switch pair 82 themselves are charged by the low voltage power supply VDC so that the first switch pair 81 and the second switch pair 82 are respectively brought to an ON state.

Next, consider where the switch control signal SCTL is at an L level. At this time, the switch control signal SCTL becomes a voltage nearly equal to the ground. The output of the inverter INV1 becomes an H level and reaches a voltage nearly equal to the low voltage power supply VDC.

Since the voltage is applied between the gate and source of the P channel MOSFET 131 of the drive circuit 13, the floating gate control circuit 1 is brought to the ON state. Since no voltage is applied between the gate and source of the N channel MOSFET 132, the floating gate control circuit 1 is brought to the OFF state. The gate-source capacitance of the third switch pair 83 itself is charged from the low voltage power supply VDC so that the third switch pair 83 is brought to an ON state.

Since no voltage is applied between the gates and sources of the P channel MOSFETs 111 and 112 of the drive circuits 11 and 12, the floating gate control circuit 1 is brought to the OFF state. Since the voltage is applied between the gates and sources of the N channel MOSFETs 112 and 122, the floating gate control circuit 1 is brought to the ON state. The gate-source capacitances of the first switch pair 81 and the second switch pair 82 themselves are discharged to the ground so that the first switch pair 81 and the second switch pair 82 are brought to an OFF state.

The floating gate control circuit 1 of the present embodiment has a feature that even when the high voltage signal is applied to the input/output terminal 101 or the input/output terminal 102, the gate-source capacitance of each switch element continues to hold the state of the electrical charge. A description will hereinafter be made of the cases where when the output switch 8 is ON and OFF, the positive high voltage signal and the negative high voltage signal are applied to the input/output terminal 101.

(A) Application of the Positive High Voltage Signal to the Input/Output Terminal 101 when the Output Switch 8 is ON:

When the switch control signal SCTL is set to the H level, the output switch 8 becomes an ON state. Under such a situation, the potential states in the floating gate control circuit 1 where the positive high voltage signal is applied to the input/output terminal 101 will be examined.

Since the first switch pair 81 and the second switch pair 82 are in the ON state when the output switch 8 is ON, their gate and source potentials follow the applied high voltage signal.

Specifically, the gate potentials of the first switch pair 81 and the second switch pair 82 are brought to a floating state by the element breakdown voltages of the high breakdown voltage diodes D1 and D2 each held in a reverse bias state, and the element breakdown voltages of the high breakdown voltage N channel MOSFETs 112 and 122 each held in an OFF state. Since the gate-source capacitances of the first switch pair 81 and the second switch pair 82 are in the state of being already charged with the electrical charge from the low voltage power supply VDC, the voltage of each gate of the first switch pair 81 and the second switch pair 82 becomes one obtained by adding the voltage of the low voltage power supply VDC to the voltage of the high voltage signal applied to the input/output terminal 101. That is, the gate-source voltages of the first switch pair 81 and the second switch pair 82 are kept at a constant voltage approximately equal to the low voltage power supply VDC. Thus, even if the positive high voltage signal is applied to the input/output terminal 101, the first switch pair 81 and the second switch pair 82 can held in the ON state.

At this time, since the third switch pair 83 is in the OFF state, the positive high voltage signal is cut off by the element breakdown voltage of the N channel MOSFET 831.

(B) Application of the Negative High Voltage Signal to the Input/Output Terminal 101 when the Output Switch 8 is ON:

When the switch control signal SCTL is set to the H level, the output switch 8 becomes an ON state. Under such a situation, the potential states in the floating gate control circuit 1 where the negative high voltage signal is applied to the input/output terminal 101 will be examined.

Since the first switch pair 81 and the second switch pair 82 are in the ON state when the output switch 8 is ON, their gate and source potentials follow the applied high voltage signal.

Specifically, the element breakdown voltages of the high breakdown voltage diodes D3 and D4 each held in the reverse bias state prevent the reverse current from the ground with respect to the gate potentials of the first switch pair 81 and the second switch pair 82. The current flows from the low voltage power supply VDC through the P channel MOSFET 111, the high breakdown voltage diode D1 and the zener diode ZD1. Likewise, the current flows from the low voltage power supply VDC through the P channel MOSFET 121, the high breakdown voltage diode D2 and the zener diode ZD2. That is, the gate-source voltages of the first switch pair 81 and the second switch pair 82 are kept at a prescribed voltage approximately equal to the zener voltage of each of the zener diodes ZD1 and ZD2. Even if the negative high voltage signal is applied, they can be maintained in the ON state.

While the third switch pair 83 is in the OFF state at this time, the gate and source potentials of the third switch pair 83 follow the negative high voltage signal due to the parasitic diode of the N channel MOSFET 831. Since the high breakdown voltage diode D5 is connected in the forward direction between the gate of the third switch pair 83 and the ground, the reverse current from the ground to the connecting node 84 is prevented. Since the MOSFET 832 is connected between the source of the third switch pair 83 and the ground, the reverse current from the ground to the connecting node 84 is prevented in like manner.

(C) Application of the Positive High Voltage Signal to the Input/Output Terminal 101 when the Output Switch 8 is OFF:

When the switch control signal SCTL is set to the L level, the output switch 8 becomes an OFF state. Under such a situation, the potential states in the floating gate control circuit 1 where the positive high voltage signal is applied to the input/output terminal 101 will be examined.

Since the first switch pair 81 is in the OFF state when the output switch 8 is OFF, the positive high voltage signal is cut off by the element breakdown voltage of the N channel MOSFET 811, so that the gate and source potentials of the first switch pair 81 and the second switch pair 82 do not reach a high voltage.

(D) Application of the Negative High Voltage Signal to the Input/Output Terminal 101 when the Output Switch 8 is OFF:

When the switch control signal SCTL is set to the L level, the output switch 8 becomes an OFF state. Under such a situation, the potential states in the floating gate control circuit 1 where the negative high voltage signal is applied to the input/output terminal 101 will be examined.

While the first switch pair 81 is in the OFF state when the output switch 8 is OFF, the gate and source potentials thereof follow the negative high voltage signal due to the parasitic diode of the high breakdown voltage N channel MOSFET 811. However, the reverse current from the ground to the gate of the first switch pair 81 is prevented by the high breakdown voltage diode D3.

The negative high voltage signal applied to the input/output terminal 101 is cut off by the first switch pair 81 inside the output switch 8. Thus, the gate and source potentials of the second switch pair 82 and the third switch pair 83 do not reach a high voltage.

The above description of (A) to (D) shows where the positive/negative high voltage signal is applied to the input/output terminal 101. Since, however, the high breakdown voltage analog switch integrated circuit 90 of the present embodiment is of the bidirectional analog switch in which the input/output terminal 101 and the input/output terminal 102 are configured symmetrically, it is operated similarly when the positive/negative high voltage signal is applied to the input/output terminal 102.

It is to be noted that the present invention is not limited to the aforementioned embodiments, but covers various modifications. While, for illustrative purposes, those embodiments have been described specifically, the present invention is not necessarily limited to the specific forms disclosed. Thus, partial replacement is possible between the components of a certain embodiment and the components of another. Likewise, certain components can be added to or removed from the embodiments disclosed.

Further note that the control lines and information lines shown above represent only those lines necessary to illustrate the present invention, not necessarily representing all the lines required in terms of products. Thus, it can be assumed that almost all the components are in fact interconnected.

What is claimed is:

1. A semiconductor switch circuit, comprising:
   a first switch pair including
      first two MOSFETs having gates connected to one another and sources connected to one another, and
      a zener diode reversely connected between the gates and sources of said first two MOSFETs;
   a second switch pair including
      second two MOSFETs having gates connected to one another and sources connected to one another, and
      a zener diode reversely connected between the gates and sources of said second two MOSFETs;
   a third switch pair comprising third two MOSFETs having gates connected to one another and sources connected to one another; and
   a floating gate control circuit which drives the first switch pair, the second switch pair, and the third switch pair,
   wherein the first switch pair and the second switch pair are connected in series between two input/output terminals through a connecting node, and
   wherein the third switch pair is connected to the connecting node between the first switch pair and the second switch pair,
   wherein the floating gate control circuit switches ON/OFF of the first switch pair, the second switch pair, and the third switch pair, based on a switch control signal inputted thereto,
   wherein, when the switch control signal is set to a first state, gate-source capacitances of the first switch pair and the second switch pair are charged from a low voltage power supply VDC by the floating gate control circuit, so that the first switch pair and the second switch pair are brought to an ON state to reach a low impedance between the two input/output terminals, and the third switch pair is turned off, and
   wherein, when the switch control signal is set to a second state, the electrical charges accumulated in the gate-source capacitances of the first switch pair and the second switch pair are discharged to ground by the floating gate control circuit, so that the first switch pair and the second switch pair are brought to an OFF state to reach a high impedance between the two input/output terminals, and the third switch pair is turned on.

2. The semiconductor switch circuit according to claim 1, wherein a combination of the first switch pair, the second switch pair, and the third switch pair is integrated in plural.

3. The semiconductor switch circuit according to claim 1, which is a bidirectional analog switch that transmits a voltage of one of the input/output terminals to the other thereof, or transmits a voltage of the other of the input/output terminals to the one thereof.

4. The semiconductor switch circuit according to claim 1, wherein the MOSFETs which configure the first switch pair and the MOSFETs which configure the second switch pair are all equal in current performance.

5. The semiconductor switch circuit according to claim 1, wherein the floating gate control circuit is supplied with a low voltage power supply lower than a maximum voltage applied to the input/output terminals.

6. The semiconductor switch circuit according to claim 5, wherein in each of the first switch pair and the second switch pair, a zener voltage of each zener diode is not less than the voltage of the low voltage power supply and not greater than a gate oxide film breakdown voltage of each MOSFET.

7. A signal processing apparatus, comprising:
a semiconductor switch circuit according to claim 1.

8. An ultrasound diagnostic apparatus, comprising:
a semiconductor switch circuit according to claim 1; and
a piezoelectric probe to which the semiconductor switch circuit is connected.

9. The semiconductor switch circuit according to claim 1, wherein the first two MOSFETs, the second two MOSFETs, and the third two MOSFETS all have a same conductivity type.

10. The semiconductor switch circuit according to claim 9, wherein said conductivity type is an N-channel conductivity type.

* * * * *